(12) United States Patent
Sung et al.

(10) Patent No.: US 9,314,520 B2
(45) Date of Patent: Apr. 19, 2016

(54) ADJUVANT COMPOSITION CONTAINING POLY-GAMMA-GLUTAMIC ACID-CHITOSAN NANOPARTICLES

(75) Inventors: Moon-Hee Sung, Daejeon (KR); Haryoung Poo, Daejeon (KR); Chul Joong Kim, Daejeon (KR); Young-Ki Choi, Cheongju-si (KR); Yong Taik Lim, Daejeon (KR); Dong Jin Jeong, Daejeon (KR); Sang-Mu Shim, Daejeon (KR)

(73) Assignees: BIOLEADERS CORPORATION, Daejeon (KR); KOOKMIN UNIVERSITY INDUSTRY-ACADEMIC COOPERATION FOUNDATION, Seoul (KR); KOREA RESEARCH INSTITUTE OF BIOSCIENCE AND BIOTECHNOLOGY, Daejeon (KR); THE INDUSTRY AND ACADEMIC COOPERATION IN CHUNGNAM NATIONAL UNIVERSITY, Daejeon (KR); CHUNGBUK NATIONAL UNIVERSITY INDUSTRY ACADEMIC COOPERATION, Cheongju-si, Chungcheongbuk-do (KR)

( * ) Notice: Subject to any disclaimer, the term of this patent is extended or adjusted under 35 U.S.C. 154(b) by 56 days.

(21) Appl. No.: 13/380,503

(22) PCT Filed: Jun. 25, 2010

(86) PCT No.: PCT/KR2010/004142
§ 371 (c)(1),
(2), (4) Date: Mar. 13, 2012

(87) PCT Pub. No.: WO2010/151076
PCT Pub. Date: Dec. 29, 2010

(65) Prior Publication Data
US 2012/0164174 A1 Jun. 28, 2012

(30) Foreign Application Priority Data
Jun. 25, 2009 (KR) .................. 10-2009-0056844

(51) Int. Cl.
*A61K 39/39* (2006.01)
*A61K 39/145* (2006.01)
*A61K 39/12* (2006.01)
*A61K 39/00* (2006.01)

(52) U.S. Cl.
CPC .............. *A61K 39/39* (2013.01); *A61K 39/12* (2013.01); *A61K 39/145* (2013.01); *A61K 2039/543* (2013.01); *A61K 2039/55583* (2013.01); *C12N 2760/16134* (2013.01)

(58) Field of Classification Search
CPC ................ A61K 2300/00; A61K 47/48315; A61K 31/74; A61K 47/48884; A61K 49/225; A61K 51/0497; A61K 9/4891; A61K 39/295; A61K 39/385; A61K 39/44; A61K 47/48892; A61K 9/209; B82Y 5/00; B82Y 15/00
See application file for complete search history.

(56) References Cited

U.S. PATENT DOCUMENTS

| | | | |
|---|---|---|---|
| 5,980,912 A | 11/1999 | Podolski et al. | |
| 6,534,065 B1 | 3/2003 | Makin et al. | |
| 2006/0134143 A1* | 6/2006 | Schneerson et al. | 424/246.1 |
| 2007/0237931 A1* | 10/2007 | Hsu | 428/204 |

FOREIGN PATENT DOCUMENTS

| | | | |
|---|---|---|---|
| CN | 10360486 A | | 2/2009 |
| KR | 10-0399091 B1 | | 9/2003 |
| KR | 10-0475406 B1 | | 3/2005 |
| KR | 10-0496606 B1 | | 6/2005 |
| KR | 10-0500796 B1 | | 7/2005 |
| KR | 10-0517114 B1 | | 9/2005 |
| KR | 10-0582120 B1 | | 5/2006 |
| KR | 10-0873179 B1 | | 12/2008 |
| WO | WO/98/42374 | * | 10/1998 |

OTHER PUBLICATIONS

Peng et al., Effects of incorporation of poly(g-glutamic acid) in chitosan/DNA complex nanoparticles on cellular uptake and transfection efficiency, 2009 (Epub Date Dec. 24, 2008), Biomaterials, vol. 30, pp. 1797-1808.*
Kohli and Alpar, Potential use of nanoparticles for transcutaneous vaccine delivery: effect of particle size and charge, 2004, International Journal of Pharmaceutics, vol. 275, pp. 13-17.*
Wang et al., "Poly(gamma-Glutamic Acid) Nanoparticles as an Efficient Antigen Delivery and Adjuvant System: Potential for an AIDS Vaccine," Journal of Medical Virology 80: 11-19 (2008) in 9 pages.
Korean Office Action dated Apr. 29, 2012 of corresponding Korean patent application No. 10-2009-0056844 (10-2010-0060489) in 5 pages.

(Continued)

*Primary Examiner* — Benjamin P Blumel
(74) *Attorney, Agent, or Firm* — Knobbe, Martens, Olson & Bear, LLP

(57) ABSTRACT

The present invention relates to an adjuvant composition containing poly-gamma-glutamic acid-chitosan nanoparticles and a vaccine composition containing the adjuvant composition, and more particularly to an adjuvant composition containing nanoparticles prepared by ionic bonding between poly-gamma-glutamic acid having ensured safety and chitosan, and a vaccine composition containing the poly-gamma-glutamic acid-chitosan nanoparticles and an antigen. The adjuvant containing the poly-gamma-glutamic acid-chitosan nanoparticles has little or no toxicity and side effects and is added to human or animal vaccines for the prevention and treatment of viral and bacterial infections and cancers to increase the production of antibodies.

5 Claims, 11 Drawing Sheets

(56) References Cited

OTHER PUBLICATIONS

Uto, Tomofumi et al., Targeting of Antigen to Dendritic Cells with Poly(γ-Glutamic Acid) Nanoparticles Induces Antigen-Specific Humoral and Cellular Immunity, J Immunol 2007, vol. 178, pp. 2979-2986.

Akagi, Takami et al., Preparation and characterization of biodegradable nanoparticles based on poly(γ-glutamic acid) with L-phenylalanine as a protein carrier, Journal of Controlled Release, 2005, vol. 108, pp. 226-236.

Ellouz, Farielle et al, Minimal Structural Requirements for Adjuvant Activity of Bacterial Peptidoglycan Derivatives, Biochemical and Biophysical Research Communications, vol. 59, No. 4, 1974, pp. 1317-1325.

Lee, Tae-Young et al., Oral administration of poly-gamma-glutamate inducesTLR4- and dendritic cell-dependent antitumor effect, Cancer Immunol Immunother, 2009, vol. 58, pp. 1781-1794.

Kim, Tae Woo et al., Oral Administration of High Molecular Mass Poly-±-Glutamate Induces NK Cell-Mediated Antitumor Immunity, Journal of Immunology, 2007; 179, pp. 775-780.

Peng, S.F., et al., Effects of incorporation of poly (gamma-glutamic acid) in chitosan/DNA complex nanoparticles on cellular uptake and transfaction efficiency. Biomaterials 30 (2009), pp. 1797-1808.

Lin, Yu-Hsin et al., Novel nanoparticles for oral insulin delivery via the paracellular pathway, Nanotechnology, 2007, vol. 18, 105102—11 pages.

Lin, Yu-Hsin et al., Preparation of Nanoparticles Composed of Chitosan/Poly-y-glutamic Acid and Evaluation of Their Permeability through Caco-2 Cells., Biomacromolecules 2005, vol. 6, pp. 1104-1112.

Lee, P.W., et al., The use of biodegradable polymeric nanoparticles in combination with a low-pressure gene gun for transdermal DNA delivery,Biomaterials 29 (2008), pp. 742-751.

Mi, F. L., et al., Oral Delivery of Peptide Drugs Using Nanoparticles Self-Assembled by Poly(y-glutamic acid) and a Chitosan Derivative Functionalized by Trimethylation, Bioconjugate Chem. 2008, 19, pp. 1248-1255.

Lin, Y.H., et al., Multi-ion-crosslinked nanoparticles with pH-responsive characteristics for oral delivery of protein drugs, Journal of Controlled Release 132 (2008), pp. 141-149.

Hsieh, C.Y., et al., Preparation of y-PGA/chitosan composite tissue engineering matrices, Biomaterials 26 (2005), pp. 5617-5623.

Song, Langzhou, et al., Efficacious Recombinant Influenza Vaccines Produced by High Yield Bacterial Expression: A Solution to Global Pandemic and Seasonal Needs, PloS ONE, May 2008, vol. 3, Issue 5, e2257, pp. 1-8.

Lee, Youn-Jeong, et al., Highly Pathogenic Avian Influenza Virus (H5N1) in Domestic Poultry and Relationship with Migratory Birds, South Korea, Emerging Infectious Disease, Mar. 2008, vol. 14, No. 3, pp. 487-490.

International Search Report dated Mar. 17, 2011 of PCT/KR2010/004142 which is the parent application—3 pages.

Chinese Office Action dated Sep. 26, 2014 for CN Patent Application No. 201080038007.2 and its English translation in 11 pages.

* cited by examiner

NP1: poly-gamma-glutamic acid + chitosan + OVA
NP2: chitosan + OVA + poly-gamma-glutamic acid

ADJUVANT COMPOSITION CONTAINING POLY-GAMMA-GLUTAMIC ACID-CHITOSAN NANOPARTICLES

TECHNICAL FIELD

The present invention relates to an adjuvant composition containing poly-gamma-glutamic acid-chitosan nanoparticles and a vaccine composition containing the adjuvant composition, and more particularly to an adjuvant composition containing nanoparticles prepared by ionic bonding between poly-gamma-glutamic acid having ensured safety and chitosan, and a vaccine composition containing the poly-gamma-glutamic acid-chitosan nanoparticles and an antigen.

BACKGROUND ART

Adjuvants are materials that can be used either for the developments of vaccines having increased antigenicity or for therapeutic and preventive purposes by enhancing non-specific immune responses to antigens. Because adjuvants function to maintain strong and rapid immune responses to antigens for a long time when the antigenic levels are low, these adjuvants are used in the preparation of vaccines. Also, the adjuvants allow special antigens to be used or the levels of antigens to be changed, thereby regulating immune responses to the antigens or controlling the types and subclasses of antibodies against the antigens. In addition, the adjuvants can be used to enhance immune responses, particularly in immunologically immature or senescent persons, in order to enhance the induction of mucous immunity.

Most of adjuvants were found in many natural materials through many trials and errors. In the first worldwide report on the adjuvants, in 1925, Ramon (France) reported that tapioca starch (Casaba) which is used in foods was mixed with diphtheria and tetanus toxoid, antigenic specificity and antibody production were effectively increased. Since then, the immune-enhancing effect of an aluminum adjuvant was reported, and an effective emulsion-type adjuvant containing inactivated killed mycobacteria as an immune modulator was developed. It is Freund's complete adjuvant (FCA) known as a very effective immune modulator, but was not suitable for human use because of its high reactogenicity. For this reason, Freund's incomplete adjuvant (FIA) containing no mycobacteria was developed and approved in Britain. Gram-negative bacterial endotoxin was reported to have an immune-enhancing effect, and the effect of muramyl dipeptide (MDP) was confirmed by Ellouz et al. in 1974 (Ellouz F. et al., *Biochem. Biophys. Res. Coomun.* 59:1317-25, 1974). Since then, it was reported that lecithin, saponin and the like can also be used as adjuvants for enhancing immunity.

An ideal adjuvant should have an immune-enhancing effect and should also be nontoxic, highly biodegradable, easy to use, easy to be available and inexpensive. Until now, many types of adjuvants have been reported, but only several types of adjuvants can be actually used in clinical practice. This is because reliable research data on safety that is the most important in the development of adjuvants for use in vaccines should be supported.

Vaccines have therapeutic and preventive effects, and thus can reduce the incidence rate of disease to 99%. Thus, vaccines are medicines that have a high effect versus cost. These days, the use of vaccines is not limited only to infectious diseases, but is being widened to various intractable diseases, including cancer and autoimmune diseases. Also, as therapeutic vaccines emerge, the development of vaccines is being recognized to be very important. Thus, the development of adjuvants as vaccine-related products is being accelerated together with the development of vaccines. As the range of immune-related diseases widens, the development of new adjuvants is being recognized as a very promising field.

Meanwhile, the present inventors acquired a patent relating to a high-molecular-weight poly-gamma-glutamic acid and the use thereof (Korean Patent Registration No. 399091), and a patent relating to a method of producing poly-gamma-glutamic acid using *Bacillus subtilis* var. chungkookjang, a salt-tolerant strain producing high-molecular-weight poly-gamma-glutamic acid (Korean Patent Registration No. 500796), as well as patents relating to an anticancer composition, an adjuvant, an immune-enhancing agent, and inhibition of viral infection (Korean Patent Registration Nos. 496606, 517114, 475406 and 0873179). In addition, the present inventors reported a hyaluronidase inhibitor containing poly-gamma-glutamic acid (Korean Patent Registration No. 582120) and found the anticancer effect based on immune-enhancing effect of poly-gamma-glutamic acid [Poo, H. R. et al., *Journal of Immunology*, 178:775, 2007, Poo, H. R. et al., *Cancer Immunol Immunother* (published online: 18 Mar. 2009)]. That is, the present inventors performed extensive studies to develop the use of poly-gamma-glutamic acid, including the medicinal use of poly-gamma-glutamic acid, thereby finding the various effects of poly-gamma-glutamic acid.

Meanwhile, polymeric nanoparticles, particularly nanoparticles made of biodegradable polymers such as poly-caprolactone, are receiving a great deal of attention due to their high biocompatibility. However, these nanoparticles have a shortcoming in that they are not suitable for delivery of hydrophilic drugs or antigens, because they are hydrophobic in nature.

Examples of the use of poly-gamma-glutamic acid for the in vivo delivery of proteins or the enhancement of humoral immunity were reported (Akagi, T. et al., *J. controlled release*, 108:226, 2005; Uto, T. et al., the *J. Imunol.*, 178: 2979, 2007). However, when poly-gamma-glutamic acid alone is used as an adjuvant, it has insufficient ability to produce an antibody. Thus, the ability of poly-gamma-glutamic acid to induce antigen-specific immunity needs to be further enhanced.

Chitosan is a cationic polysaccharide that is a deacetylated form of chitin and it is nontoxic and highly biocompatible. Also, chitosan is known as a material that can open the tight junction between cells, and thus is highly effective in mucosal drug delivery systems. Most chitosans have a molecular weight of 50-2,000 kDa and dissolve in an acetic acid solution (pH 4). However, in order to allow chitosan to be applied as medicinal materials, chitosan should be kept in an aqueous solution at neutral pH. In order to maintain chitosan in a cationic aqueous solution at physiological pH, treating chitosan with cellulase to reduce the molecular weight is necessary.

A complex of poly-gamma-glutamic acid and chitosan nanoparticles is an ionically bonded complex of poly-gamma-glutamic acid and chitosan and is used either as a carrier for oral delivery of insulin or DNA delivery, but the use thereof in the induction of immune responses was not reported (Lin, Y. et al., *Biomacromolecules*, 6:1104, 2005; Lin, Y. et al., *Nanotechnology*, 16:105102, 2007).

Accordingly, the present inventors have made extensive efforts to overcome the above-described problems occurring in the prior art and, as a result, have found that, when an adjuvant containing nanoparticles prepared by ionic bonding between poly-gamma glutamic acid and chitosan is administered to mice together with various antigens, the production of antibodies significantly increases compared to when poly-gamma-glutamic acid alone is used as an adjuvant, thereby completing the present invention.

DISCLOSURE OF INVENTION

It is an object of the present invention to provide an adjuvant composition containing poly-gamma-glutamic acid-chitosan nanoparticles having excellent ability to induce antigen-specific immune responses.

Another object of the present invention is to provide a vaccine composition containing poly-gamma-glutamic acid-chitosan nanoparticles and an antigen.

Still another object of the present invention is to provide a method for preparing a vaccine containing poly-gamma-glutamic acid-chitosan nanoparticles and an antigen.

To achieve the above objects, the present invention provides an adjuvant composition containing poly-gamma-glutamic acid-chitosan nanoparticles.

The present invention also provides a method of increasing the production of an antibody against an antigen by administering the adjuvant composition together with the antigen to animals, excluding humans.

The present invention also provides a vaccine composition containing poly-gamma-glutamic acid-chitosan nanoparticles and an antigen.

The present invention also provides a method for preparing a vaccine comprising poly-gamma-glutamic acid-chitosan nanoparticles ionically bonded to an antigen having a negatively charged surface, the method comprising the steps of: (a) ionically bonding chitosan to an antigen having a negatively charged surface; and (b) adding poly-gamma-glutamic acid to the antigen bonded to the chitosan to form an ionic bond between the chitosan and the poly-gamma-glutamic acid, thereby preparing a vaccine comprising poly-gamma-glutamic acid-chitosan nanoparticles and the antigen.

The present invention also provides a method for preparing a vaccine comprising poly-gamma-glutamic acid-chitosan nanoparticles ionically bonded to an antigen having a positively charged surface, the method comprising the steps of: (a) ionically bonding poly-gamma-glutamic acid to an antigen having a positively charged surface; and (b) adding chitosan to the antigen bonded to the poly-gamma-glutamic acid to form an ionic bond between the poly-gamma-glutamic acid and the chitosan, thereby preparing a vaccine comprising poly-gamma-glutamic acid-chitosan nanoparticles and the antigen.

The present invention also provides a method of increasing the production of an antibody against to an antigen by administrating the vaccine composition to animals, excluding humans.

Other features and embodiments of the present invention will be more apparent from the following detailed descriptions and the appended claims

BEST MODE FOR CARRYING OUT THE INVENTION

Figure 1:
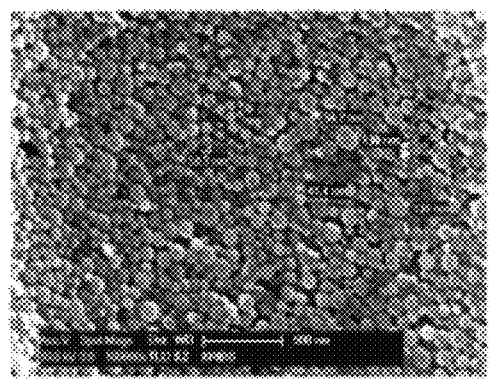
FIG. 1 is a micrograph of poly-gamma-glutamic acid-chitosan nanoparticles.

The present invention is directed to an adjuvant composition containing poly-gamma-glutamic acid-chitosan nanoparticles and a vaccine composition containing poly-gamma-glutamic acid-chitosan nanoparticles and an antigen.

In the present invention, nanoparticles formed by electrostatic interaction between the negative charge of the carboxyl reactive group of poly-gamma-glutamic acid and the protonated positive charge of the amino reactive group of chitosan were used as poly-gamma-glutamic acid-chitosan nanoparticles.

Because the poly-gamma-glutamic acid-chitosan nanoparticles according to the present invention are prepared by simple electrostatic interaction without crosslinking between proteins harmful to the human body, these nanoparticles have very high safety and effectiveness, and thus are suitable for use as an adjuvant.

Poly-gamma-glutamic acid is a viscous amino acid polymer consisting of D and L-glutamic acids linked by gamma-glutamyl bonds and is a natural amino acid material by *Bacillus* sp. strains. In one aspect of the present invention, the poly-gamma-glutamic acid was prepared by fermenting *Bacillus substilis* chungkookjang (KCTC 0697BP) and had an average molecular weight of 1-15,000 kDa.

In the present invention, the poly-gamma-glutamic acid may be cleaved to fragments having a desired molecular weight by a suitable method or separated into fragmented into fragments having a desired molecular weight by a suitable method.

An adjuvant containing poly-gamma-glutamic acid-chitosan nanoparticles according to the present invention according to the present invention are prepared by simple ionic bonding rather than chemical bonding between poly-gamma-glutamic acid, which is a biopolymer produced by fermentation of *Bacillus substilis* chungkookjang and chitosan, and chitosan, and thus is an adjuvant material having high safety, biocompatibility and antibody-producing ability.

The molecular weight of the poly-gamma-glutamic acid that is used in the preparation of the poly-gamma-glutamic acid-chitosan nanoparticles according to the present invention is preferably 50-15,000 kDa. If the molecular weight of the poly-gamma-glutamic acid is less than 50 kDa, the immune enhancing effect thereof will be low, and if the molecular weight of the poly-gamma-glutamic acid is more than 15,000 kDa, it can have problems associated with increased viscosity.

In the present invention, the molecular weight of chitosan is preferably 500-1,000 kDa. If the molecular weight of chitosan is less than 500 Da, it will be difficult to prepare chitosan nanoparticles, and if the molecular weight of chitosan is more than 1000 kDa, it will have low solubility in a neutral aqueous solution.

In the present invention, nanoparticles having a negatively charged surface can be prepared by increasing the ratio of poly-gamma-glutamic acid in the preparation of the poly-gamma-glutamic acid-chitosan nanoparticles.

In the present invention, the surface of the poly-gamma-glutamic acid may be negatively charged.

The poly-gamma-glutamic acid-chitosan nanoparticles according to the present invention are not prepared by a chemical method, but are prepared by a simple ionic reaction, and thus are less toxic and have high safety.

In the adjuvant composition containing the poly-gamma-glutamic acid-chitosan nanoparticles according to the present invention, the poly-gamma-glutamic acid-chitosan nanoparticles may be contained in an amount of 0.001-5 parts by weight, and preferably 0.01-3 parts by weight, based on 100 parts by weight (dry weight) of the vaccine composition. If the poly-gamma-glutamic acid-chitosan nanoparticles are contained in an amount of less than 0.001 parts by weight based on 100 parts by weight (dry weight) of the vaccine composition, the composition cannot have the ability to produce antibody, and if it is contained in an amount of more than 5 parts by weight, the viscosity of the composition will excessively increase.

In the present invention, the antigen that is contained in the vaccine composition may be selected from among proteins, peptides, nucleosides, nucleotides, viruses, antiviral agents, anti-tumor agents, antibiotics and anti-inflammatory agents.

In the present invention, the vaccine composition may be used for the prevention or treatment of a disease caused by any one or more viruses selected from among avian influenza virus, swine influenza virus and novel influenza virus. Also, it may be used for the prevention or treatment of any one or more diseases selected from the group consisting of cervical cancer, skin melanoma, prostate cancer, colon cancer, lung cancer, breast cancer, ovarian cancer, head and neck cancer, vulvar cancer, bladder cancer, brain cancer, and glioma.

In another aspect, the present invention is directed to a method for preparing a vaccine comprising poly-gamma-glutamic acid-chitosan nanoparticles ionically bonded to an antigen having a negatively charged surface, the method comprising the steps of: (a) ionically bonding chitosan to an antigen having a negatively charged surface; and (b) adding poly-gamma-glutamic acid to the antigen bonded to the chitosan to form an ionic bond between the chitosan and the poly-gamma-glutamic acid, thereby preparing a vaccine comprising poly-gamma-glutamic acid-chitosan nanoparticles and the antigen.

In the preparation of the poly-gamma-glutamic acid-chitosan nanoparticles according to the present invention, if an antigen or virus to be bonded has a positive charge, poly-gamma-glutamic acid is first bonded to the antigen or virus, and then chitosan is bonded, and if the antigen or virus has a negative charge, chitosan is first is bonded thereto and then poly-gamma-glutamic acid is added thereto, whereby the resulting poly-gamma-glutamic acid-chitosan nanoparticles can more effectively function as an adjuvant.

In still another aspect, the present invention is directed to a method for preparing a vaccine comprising poly-gamma-glutamic acid-chitosan nanoparticles ionically bonded to an antigen having a positively charged surface, the method comprising the steps of (a) ionically bonding poly-gamma-glutamic acid to an antigen having a positively charged surface; and (b) adding chitosan to the antigen bonded to the poly-gamma-glutamic acid to form an ionic bond between the poly-gamma-glutamic acid and the chitosan, thereby preparing a vaccine comprising poly-gamma-glutamic acid-chitosan nanoparticles and the antigen.

In yet another aspect, the present invention is directed to a method of increasing the production of an antibody against an antigen by administering the adjuvant composition together with the antigen or administering the vaccine composition to animals, excluding humans.

In the present invention, the administering is performed by any one selected from the group consisting of subcutaneous injection, intramuscular injection, intracutaneous injection, intraperitoneal injection, intranasal administration, oral administration, and transdermal administration.

Examples of carriers, excipients and diluents that can be contained in the adjuvant composition or vaccine composition containing poly-gamma-glutamic acid-chitosan nanoparticles composition include lactose, dextrose, sucrose, sorbitol, mannitol, xylitol, malitol, starch, glycerin, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil. For formulations, commonly used diluents or excipients such as fillers, expanders, binders, wetting agents, disintegrants and surfactants, etc., may be used. Formulations for parenteral administration include sterilized aqueous solutions, non-aqueous solvents, suspensions, emulsions, lyophilized agents, suppositories, etc. Non-aqueous solvents and suspensions may be prepared using propylene glycol, polyethylene glycol, vegetable oils such as olive oil, or injectable esters such as ethyloleate.

The dose of the adjuvant containing the poly-gamma-glutamic acid-chitosan nanoparticles according to the present invention may vary depending on the subject's age, sex and weight, the route of administration, and the severity of disease.

In addition, the poly-gamma-glutamic acid-chitosan nanoparticles of the present invention may be added to medicinal compositions comprising preventive or therapeutic vaccines which are used for the prevention and treatment of cancers, particularly skin melanoma, prostate cancer, colon cancer, lung cancer, breast cancer, ovarian cancer, head and neck cancer, vulvar cancer, bladder cancer, brain cancer, and glioma, as well as non-infectious chronic diseases.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Ultra-High-Molecular-Weight Poly-Gamma-Glutamic Acid

A basal medium (supplemented with 3% L-glutamic acid; containing glucose 3%, $(NH_4)_2SO_4$ 1%, $KH_2PO_4$ 0.27%, $Na_2HPO_4.12H_2O$ 0.17%, NaCl 0.1%, sodium citrate 0.5%, soypeptone 0.02%, $MgSO_4.7H_2O$ 0.7%, vitamin solution 10 ml/L, pH 6.8) for production of poly-gamma-glutamic acid was prepared and sterilized. A culture broth (LB medium) of *Bacillus subtilis* var chungkookjang (KCTC 0697BP) was inoculated into the medium in a 5-L Jar fermentor (working vol. 3 L) at a concentration of 4% and fermented at an agitation rate of 500 rpm, an air injection rate of 1.0 vvm and 37° C. for 48 hours. Then, the bacterial cells were removed using a small filter press (1% celite), and the remaining material was used as a sample solution containing poly-gamma-glutamic acid.

The sample solution containing poly-gamma-glutamic acid was adjusted to pH 2.0 with a 2 N sulfuric acid solution, and then allowed to stand at 10° C. or below for 15 hours, thereby obtaining a poly-gamma-glutamic acid precipitate. The resulting material was washed with a sufficient amount of cold distilled water (10° C. or below) having a pH of 3.5 or more, and then filtered through a Nutsche filter to collect a poly-gamma-glutamic acid which was then freeze-dried, thereby preparing an ultra-high-molecular-weight poly-gamma-glutamic acid.

Example 2

Preparation of Poly-Gamma-Glutamic Acid-Chitosan Nanoparticles

Using the poly-gamma-glutamic acid prepared in Example 1 and chitosan (Amicogen Co., Korea), nanoparticles to be used as an adjuvant were prepared.

Specifically, the poly-gamma-glutamic acid and chitosan were dissolved in a 0.85% NaCl solution. The poly-gamma-glutamic acid solution and the chitosan solution were mixed with each other at a ratio of 1:1-8:1 (poly-gamma-glutamic acid: chitosan), thereby preparing poly-gamma-glutamic acid-chitosan nanoparticles having a negatively charged surface. The particle size and surface charge of the prepared nanoparticles were measured using DLS (Dynamic Light Scattering). As a result, it was seen that the prepared nanoparticles had a particle size of 200-300 nm and a surface charge of −20.8 mV. In addition, the surface morphology of the prepared nanoparticles was observed with an electron microscope (see FIG. 1).

TABLE 1

Particle size and surface charge of poly-gamma-glutamic acid-chitosan nanoparticles

| | Particle size (nm) | surface charge (mV) |
|---|---|---|
| poly-gamma-glutamic acid-chitosan nanoparticles (negative charge) | 263 | −20.8 |

Example 3

Preparation of Poly-Gamma-Glutamic Acid-Chitosan Nanoparticles Using Various Orders of Addition of Target Protein In order to verify whether the poly-gamma-glutamic acid-chitosan nanoparticles prepared in Example 2 function as an adjuvant for increasing the production of an antibody to a corresponding protein, the pI value of the corresponding protein was examined and nanoparticles were prepared using various orders of addition of the protein. First, OVA-FITC obtained by bonding the fluorescent material FITC to an OVA protein (SIGMA, USA) having a pI value of 5.2 was bonded to poly-gamma-glutamic acid-nanoparticles. Specifically, the following two kinds of nanoparticles were prepared: nanoparticles prepared by mixing poly-gamma-glutamic acid with OVA-FITC, then adding chitosan thereto; and nanoparticles prepared by mixing chitosan with OVA-FITC, and then adding poly-gamma-glutamic acid thereto. The degree of bonding of OVA in the prepared nanoparticles was observed with a fluorescence microscope.

Figure 2:
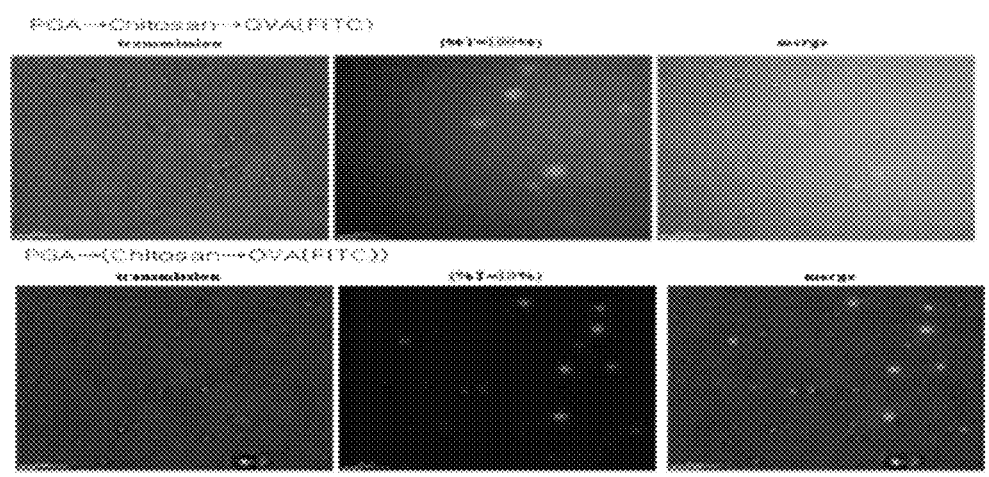
FIG. 2 is a set of confocal laser fluorescence micrographs of poly-gamma-glutamic acid-chitosan nanoparticles introduced with FITC-labeled OVA in order to examine the rate of introduction of an antigenic protein according to the order of addition of the protein.

As a result, as shown in FIG. 2, the nanoparticle sample prepared by mixing chitosan with OVA-FITC and then adding poly-gamma-glutamic acid thereto showed lighter fluorescence on the surface and inside thereof. This was believed to be because OVA had a negative charge at neutral pH, and thus a larger amount of OVA was introduced into the nanoparticle sample prepared by bonding OVA to positively charged chitosan and then adding poly-gamma-glutamic acid.

Example 4

Enhancement of Production of OVA-Specific Antibody by Poly-Gamma-Glutamic Acid-Chitosan Nanoparticles In this Example, in order to examine the poly-gamma-glutamic acid-chitosan nanoparticles of the present invention show the effect of enhancing immunity specific for OVA antigen, the effects of the nanoparticles on B cell-mediated humoral immune responses (associated with antibody production) among antibody-specific immune responses were examined.

First, in a control, OVA (100 μg) was mixed with a poly-gamma-glutamic acid having a molecular weight of 5,000 kDa and injected into the abdominal cavity of C57/BL6 mice. In test groups, each of poly-gamma-glutamic acids having molecular weights of 50 kDa, 500 kDa, 2,000 kDa, 5,000 kDa and 7,000 kDa was mixed with chitosan to prepare nanoparticles which were then mixed with OVA (100 μg) and injected into the abdominal cavity of C57/BL6 mice.

Also, a poly-gamma-glutamic acid having a molecular weight of 7,000 kDa was used to prepare poly-gamma-glutamic acid-chitosan nanoparticles using various orders of addition of a target protein. Specifically, the following nanoparticles were prepared: nanoparticles prepared by mixing poly-gamma-glutamic acid with chitosan and then adding OVA thereto; and nanoparticles prepared by mixing chitosan with OVA and then adding poly-gamma-glutamic acid thereto. As a control, OVA was injected together with poly-gamma-glutamic acid or CFA.

Each of the samples was injected into the abdominal cavity of mice twice once a week, and mouse serum was collected at 3 weeks after the injection, and the antibody titer against OVA in the serum was measured by ELISA (enzyme linked immunosorbent assay).

In the ELISA assay, a plate coated with OVA (0.5 μg/ml) was blocked with PBS/5% skim milk, after which the sera of the control group and the test groups were serially diluted to various concentrations and cultured on the plate at 37° C. Then, horseradish peroxidase-conjugated mouse-IgG antibody (specific for Fc) was added thereto. The blocking of the plate and the addition of the mouse-IgG antibody were performed for 1 hour, and the sera were incubated for 2 hours. After each of the above-mentioned steps, washing with PBS/0.05% Tween 20 was performed three times. As a substrate, 100 μl of TMB (tetramethylbenzidine (BD Biosciences, USA) was added to develop a reaction, and then the absorbance at 450 nm was measured with an ELISA reader.

Figure 3:
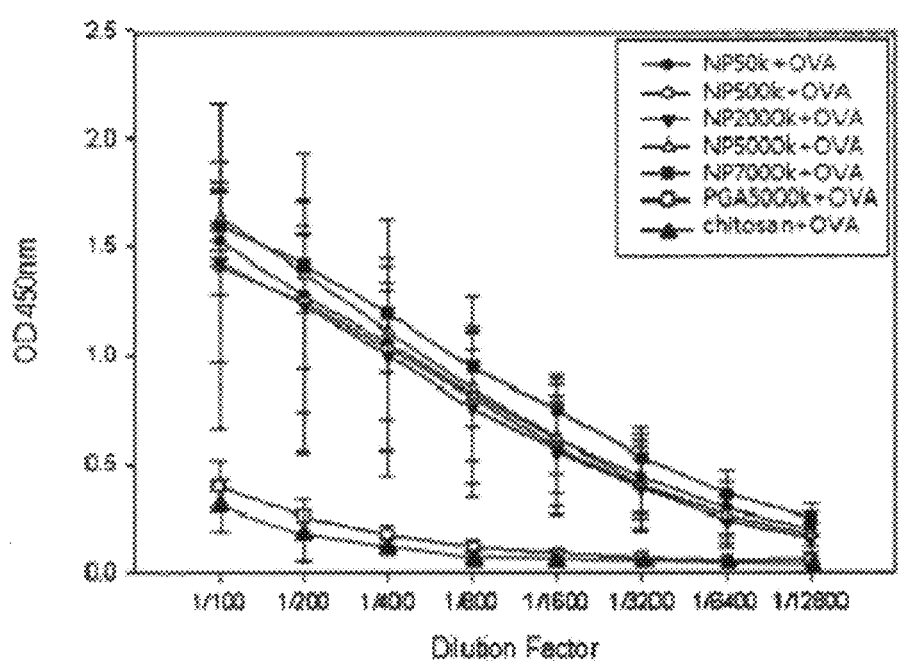
FIG. 3 show the results of determining the production of an OVA-specific antibody by measuring OVA-specific serum IgG after mixing OVA with poly-gamma-glutamic acid (PGA)-chitosan nanoparticles containing various molecular weights of PGA in order to observe the effect of OVA antigen on humoral immunity.

As a result, as shown in FIG. 3, the antibody titer against OVA in the mice injected with the poly-gamma-glutamic acid-chitosan nanoparticles (having various molecular weights) together with OVA was significantly higher than the antibody titer against OVA in the mice injected with the mixture of OVA with poly-gamma-glutamic acid.

Figure 4:
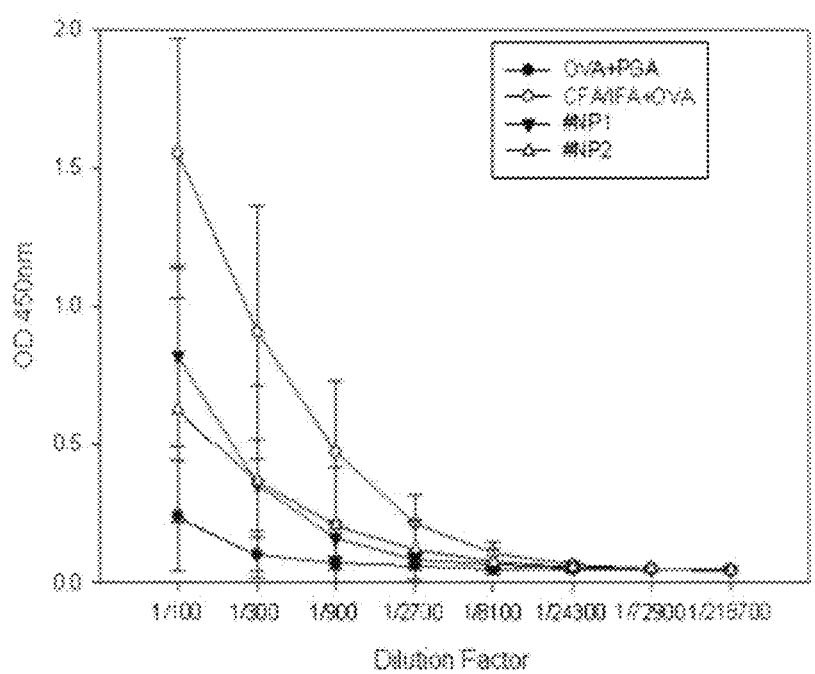
FIG. 4 shows the results of observing the production of OVA-specific antibody and measuring the production of OVA-specific serum IgG for comparison with Freund adjuvant after injecting into mice a mixture of OVA with poly-gamma-glutamic acid-chitosan nanoparticles having various charges.

Also, as shown in FIG. 4, the antibody titer in the mice injected with the nanoparticles prepared by mixing chitosan with poly-gamma-glutamic acid and then adding OVA was similar to the antibody titer in the mice injected with the nanoparticles prepared by mixing chitosan with OVA and then adding poly-gamma-glutamic acid thereto.

Example 5

Enhancement of Cell-Mediated Immune Responses by Poly-Gamma-Glutamic Acid-Chitosan Nanoparticles The cell-mediated immune responses of T-cells to OVA in the mouse spleen by poly-gamma-glutamic acid-chitosan nanoparticles were examined. Form the mice treated in Example 4, 5 mice per group were selected and the spleen was removed from each of the mice. The spleen tissue was transferred into a sterilized Petri dish and ground using a cell strainer, and cells were isolated from the ground tissue capsule. All the contents in the Petri dish were transferred into a 15-ml tube which was filled with RPMI medium. Then, the content in the tube was centrifuged at 1,500 rpm for 5 minutes, and the supernatant was removed. 3 ml of red blood cell lysing buffer (Sigma Aldrich, Germany) was added to the pellets which were then allowed to stand in a water tank at 37° C. for 10 minutes, lysing the red blood cells. The cells in the tube were washed with PBS, and then suspended in RPMI 1640 medium to separate the splenocytes. The separated splenocytes were plated on a 24-well plate at a density of $1\times10^6$ cells/ml and treated with 2 μl of golgi plug and 1 μg/ml of MHC class I-restricted OVA peptide for 12 hours. Then, the cells were stained with a CD8-specific antibody (PE-conjugated anti-mouse CD8), which is a T cell surface molecule, at 4° C. for 1 hour. Then, the cells were perforated with a Cytofix/Cytoperm kit (BD Biosciences, USA), and IFN-γ in the cells was stained with an IFN-γ-specific antibody (FITC conjugated anti-mouse IFN-γ).

Figure 5:
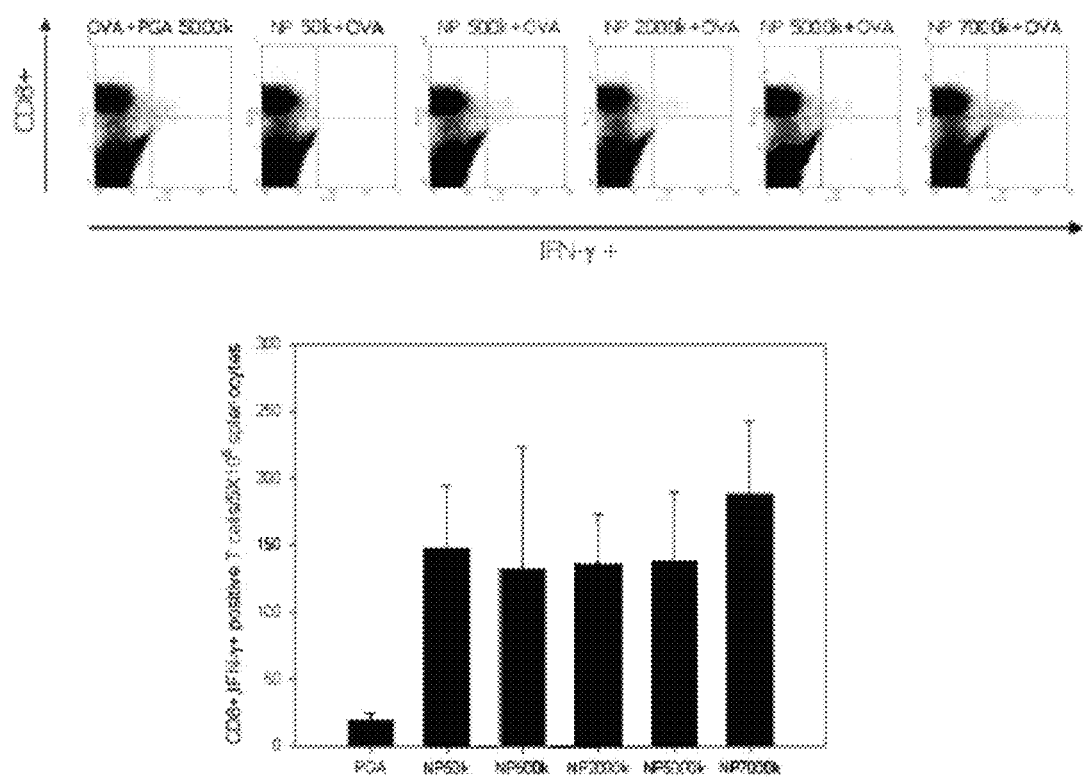
FIG. 5 shows the results of FACS analysis of the activation of IFN-γ-secreting CD8+ T cells by PGA-chitosan nanoparticles containing various molecular weights of PGAs, conducted to examine the cellular immune response of T cells in the mouse spleen to OVA by poly-gamma-glutamic acid-chitosan nanoparticles.

As a result, as shown in FIG. 5, the poly-gamma-glutamic acid-chitosan nanoparticles (containing various molecular weights of poly-gamma-glutamic acid) promoted the activation of the IFN-γ-secreting CD8+ T cells compared to the control group.

Figure 6:
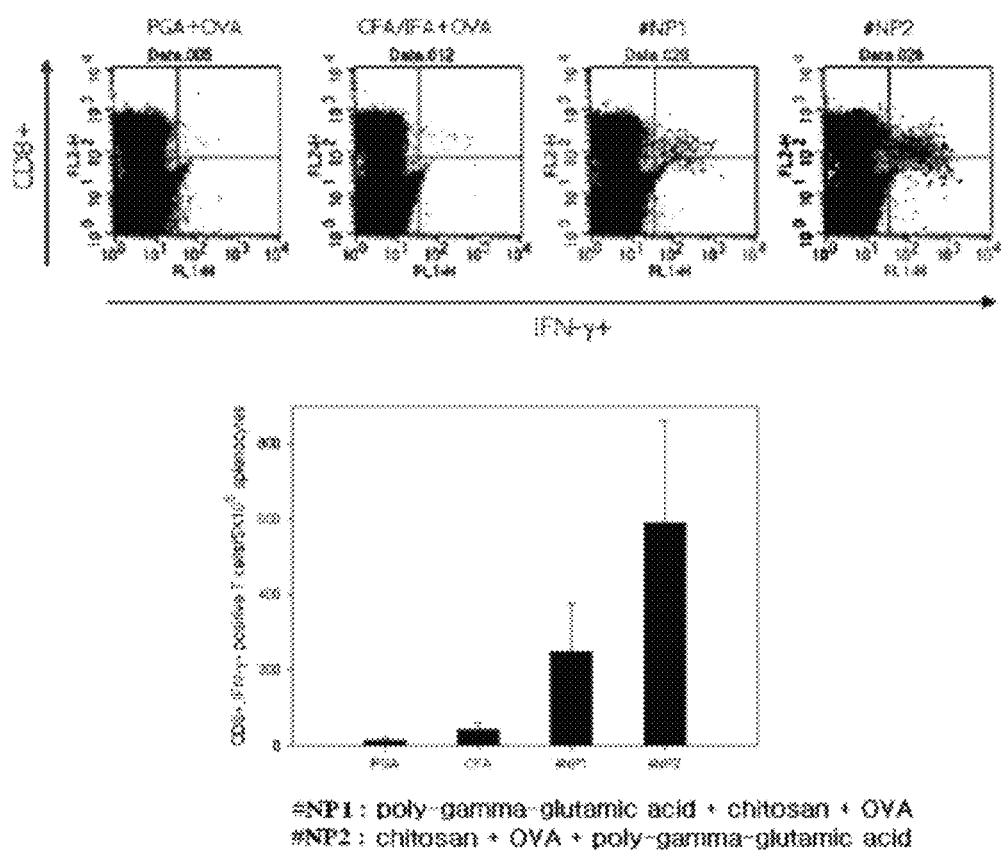
FIG. 6 shows the results of FACS analysis of the distribution of IFN-γ-secreting CD8+ T cells, conducted to examine the activation of T cells according to the mixing ratio of dentritic cells with T cells by poly-gamma-glutamic acid-chitosan nanoparticles prepared in various mixing orders.

Also, in the case of the nanoparticles prepared using various orders of addition of the antigenic protein, as shown in FIG. 6, the nanoparticles prepared by mixing chitosan with OVA and then adding poly-gamma-glutamic acid thereto had a higher ability to induce the activation of the IFN-γ-secreting CD8+ T cells than the nanoparticles prepared by mixing poly-gamma-glutamic acid with chitosan and then adding OVA thereto (see FIG. 6).

Example 6

Enhancement of Cell-Mediated Immune Responses to AI Protein by Poly-Gamma-Glutamic Acid-Chitosan Nanoparticles In this Example, in order to examine whether the poly-gamma-glutamic acid-chitosan nanoparticles of the present invention show the effect of enhancing immunity specific the antigenic protein HA (hemagglutinin) specific for avian influenza virus (AIV), the effects of the nanoparticles on B cell-mediated humoral immune responses (associated with antibody production) among antibody-specific immune responses were examined.

The HA protein in the experiment was a HA (hemagglutinin) known to have a major epitope for the neutralizing antibody of avian influenza virus [A/chicken/Korea/IS2/2006 (H5N1))] (Yong-Jeong Lee et al. *Emerging Infectious Diseases.* 2008. 14:487-490). Specifically, it was prepared by synthesizing a gene corresponding to Genbank accession No. EU233683 by PCR, inserting the synthesized gene into an *E. coli* expression vector (pRSET), expressing a recombinant antigenic protein in the *E. coli* and purifying the antigenic protein (Langzhou Song et al. *PLoS ONE,* 2008. e2257).

As a control group, HA protein (7.128 μg) alone was injected subcutaneously or administered nasally into mice. In a test group, nanoparticles prepared by mixing poly-gamma-glutamic acid having a molecular weight of 7,000 kDa with chitosan were mixed with HA protein (7.128 μg) and injected subcutaneously or administered nasally into mice.

After the first subcutaneous injection or nasal administration, the mice sera were collected at 1-week intervals, and the antibody titer against HA protein in the sera was measured by ELISA (enzyme linked immunosorbent assay).

In the ELISA assay, a plate coated with HA protein was blocked with PBS/5% fetal bovine serum, and then the sera of the control group and the test group were incubated at various dilution ratios. Then, Horseradish peroxidase-conjugated mouse-IgG antibody (specific for Fc) was added thereto. All the incubations were performed at 37° C. for 1 hours, and after each of the above-mentioned steps, washing with PBS/ 0.05% Tween 20 was performed three times. As a substrate, 1 mg/ml of ABTS (2,2-azinobis(3-ethylbenzthiazolinesulfonic acid)) was added to develop a reaction, and after 30 minutes, the absorbance at 450 nm was measured with an ELISA reader.

Figure 7:
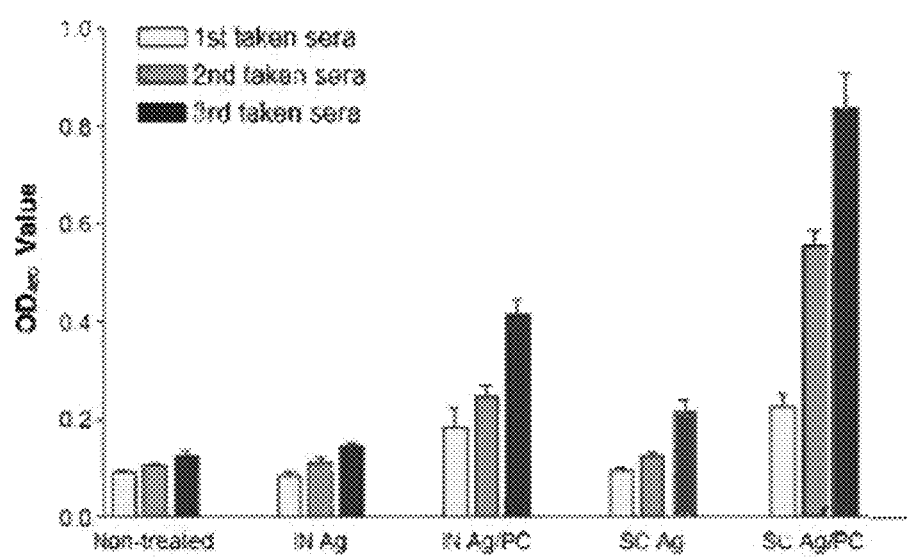
FIG. 7 shows the results of measuring AI-specific serum IgG after subcutaneously injecting a mixture of AI protein and poly-gamma-glutamic acid-chitosan nanoparticles into mice or administering the mixture into the nasal cavity of mice in order to examine the production of AI protein-specific antibody.

As a result, as shown in FIG. 7, the antibody titer against HA protein in the mice injected subcutaneously or administered nasally with the poly-gamma-glutamic acid-chitosan nanoparticles together with HA protein was higher than the antibody titer in the mice injected subcutaneously or administered nasally with HA protein alone.

Example 7

Ability of Poly-Gamma-Glutamic Acid-Chitosan Nanoparticles to Induce Neutralizing Antibody The measurement of antibody titer in the sera of mice of each group was measured by a HI (haema-gglutination inhibition) test method in the following manner.

All the sera were treated with a 3-fold volume of RDE (receptor-destroying enzyme) (for example, addition of 30 µl of RDE to 10 µl of serum) extracted from *Vibrio cholerae*, after which the sera were cultured in an incubator at 37° C. for 18-20 hours. The sample obtained by removing the activities of non-specific receptors from the serum was serially 2-fold diluted by 25 µl each time in a 96-well round bottom flask. Then, the same volume of 4 HAU was added to the serum sample which was then incubated at 37° C. for 30 minutes. Finally, 50 µl of 0.5% chicken red blood cell-containing PBS was added thereto and incubated at room temperature for 40 minutes. The antibody titer was calculated in 50 µl of the diluted serum and expressed as the N value in $\log_{10} N=10^N$.

Figure 8:
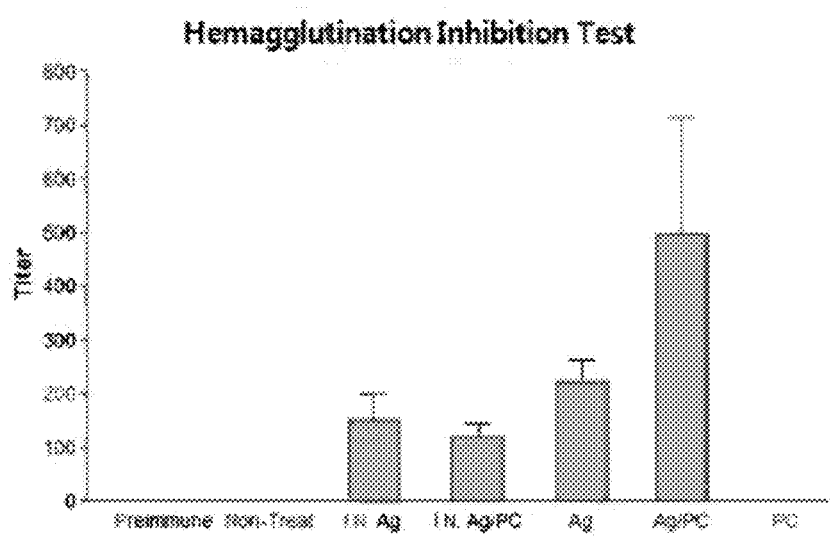
FIG. 8 shows the results of measuring antibody titer in mouse serum using a HI (Haemagglutination Inhibition) test method in order to examine the neutralizing antibody-inducing ability of poly-gamma-glutamic acid-chitosan nanoparticles.

As a result, as shown in FIG. 8, the antibody titer against virus increased in the test group injected subcutaneously or administered nasally with the poly-gamma-glutamic acid-chitosan nanoparticles and AI protein.

Example 8

Effect of Poly-Gamma-Glutamic Acid-Chitosan Nanoparticles on Enhancement of Immunity Against Virus In this Example, in order to examine the immune-enhancing effect of the poly-gamma-glutamic acid-chitosan nanoparticles, the death of test animals infected with influenza virus was observed.

(1) Preparation of Virus

Influenza virus used as a pathogen was an H1N1 influenza virus strain (A/Puerto Rico/8/34(H1N1)) showing high pathogenicity in mice, provided by professor Young-Ki Choi, Department of Microbiology, College of Medicine, Chungbuk National University. The virus strain was amplified in Madin-Darby canine kidney (MDCK) cells and then used in the experiment. As test animals, 6-week-old female Balb/C mice were used.

The purification of the viral strain was performed in the following manner.

First, the isolated virus was diluted in antibiotic-containing PBS and inoculated into the fertilized egg of a 10-day-old white leghorn chicken. Then, the fertilized virus was stationary-incubated at 37° C. for 48 hours, after which the allantoic fluid of the fertilized egg was taken to obtain amplified virus.

Meanwhile, MDCK cells were grown alpha-MEM (minimum essential medium, Gibco, USA) containing penicillin, streptomycin and 5% fetal bovine serum (FBS) in a 6-well cell culture plate and were washed three times with PBS. Then, the cells were diluted with FBS-free medium containing penicillin and streptomycin (hereinafter referred to as "P/S"), and each well of the plate was infected with the diluted virus and then incubated in a 5% $CO_2$ incubator at 37° C. for 1 hour. FBS-free alpha-MEM medium containing 0.1% TPCK (N-alpha-tosyl-L-phenylalanyl chloromethyl ketone) treated-trypsin EDTA and P/S was added to each well and incubated in an incubator. After 24 hours of incubation, the cell culture plate was washed with PBS and fixed with 0.1% noble agar-containing medium.

The cultured plaque was inoculated into each well of a 24-well plate in which MDCK cells were cultured, and FBS-free alpha-MEM medium containing 0.1% TPCK treated-trypsin EDTA and P/S was added to each well of the plate and incubated in an incubator. After 48 hours, the medium in each well was taken and centrifuged, and the supernatant was infected into a MDCK cell flask prepared in the same manner as described above. Then, the cells were cultured for 36-48 hours, and the cell culture was centrifuged. The supernatant was transferred into microtubes and stored in a freezer at −80° C. until use in an animal test.

(2) Animal Test

In a control group, mice injected subcutaneously or administered nasally with influenza virus alone were used. In a test group, the poly-gamma-glutamic acid-chitosan nanoparticles were mixed with AI antigenic protein and injected subcutaneously or administered nasally into mice, and on the next day, the mice were infected with influenza virus.

For infection with the virus, the test animals were anesthetized with diethyl ether for 30 seconds, and then 30 µl of the virus ($1.25 \times 10^5$ $EID_{50}$) was administered into the nasal cavity of each mouse.

Figure 9:
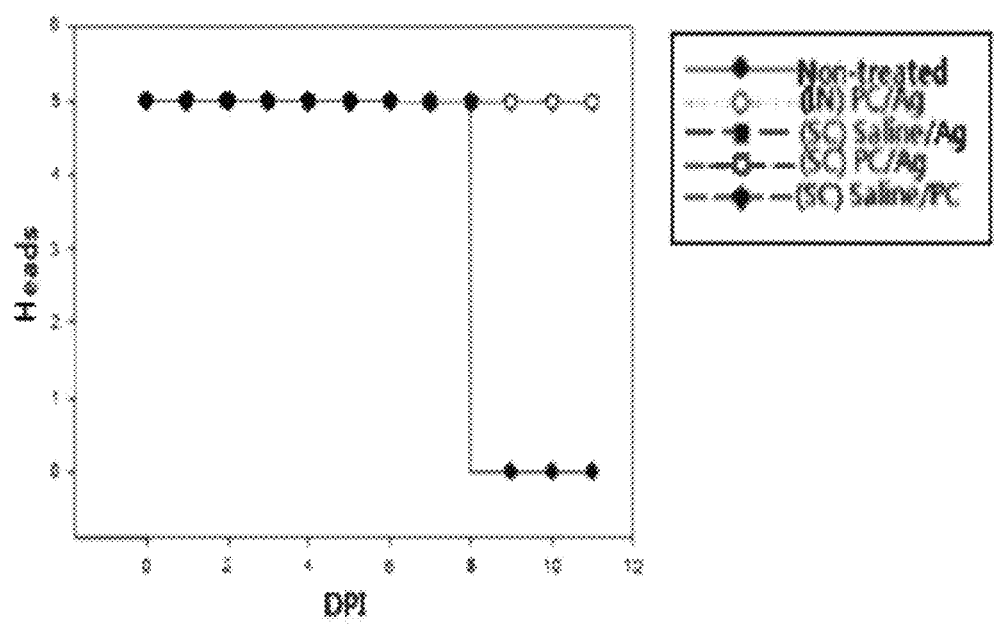
FIG. 9 is a graphic diagram showing the change in the number of deaths in virus-infected mice over time after the subcutaneous injection or nasal administration of poly-gamma-glutamic acid-chitosan nanoparticles, observed in order to examine the antibody producing ability of the nanoparticles.

As a result, as shown in FIG. 9, all the mice in the control group were dead 8 days after administration of the virus, but in the case of the group administered with the mixture of the poly-gamma-glutamic acid-chitosan nanoparticles with AI protein, all the mice survived up to 11 days after administration of the virus. Thus, it was concluded that the poly-gamma-glutamic acid-chitosan nanoparticles induced the production of an antibody against AI protein to inhibit infection with the virus, whereby the mice survived.

Example 9

Effect of Poly-Gamma-Glutamic Acid-Chitosan Nanoparticles on Enhancement of Immunity Against Influenza Virus In this Example, in order to examine the effect of the poly-gamma-glutamic acid-chitosan nanoparticles on the enhancement of immunity against influenza virus, the adjuvant effect of the poly-gamma-glutamic acid-chitosan nanoparticles on an influenza vaccine was examined.

(1) Influenza Vaccine

An influenza vaccine used as an antigen was a vaccine antigen of the H1N1 influenza virus strain (A/California/07/09 (H1N1)).

(2) Test Animals

In a control group, mice injected intramuscularly with PBS alone. In test groups, the following mice were used: mice injected intramuscularly with the influenza vaccine (0.2 µg) alone; mice injected intramuscularly with a mixture of the influenza vaccine (0.2 µg) with alum adjuvant; and mice injected intramuscularly with a mixture of the influenza vaccine (0.2 µg) and the poly-gamma-glutamic acid-chitosan nanoparticles (800 µg).

For vaccination, each sample was intramuscularly injected twice at 2-week intervals (day 0 and day 14). 14 days after vaccination, the sera were collected and the titer against the influenza vaccine antigen in the sera was measured by ELISA (enzyme linked immunosorbent assay).

In the ELISA assay, a plate coated with the influenza vaccine antigen was blocked with PBS/1% BSA, and all the sera of the control group and the test groups were incubated at various dilution ratios. Then, each of horseradish peroxidase-conjugated mouse-IgG antibody, IgG2a antibody and IgG1 antibody was added thereto. All the incubations were performed at 37° C. for 1 hour, and after each step, the plate was washed three times with PBS/0.05% Tween 20. As a substrate, 100 µl of a 1:1 mixture of TMB (3,3',5,5' tetramethylbenzidine) A solution and B solution was added to develop a reaction, after which 50 µl of 0.5N $H_2SO_4$ solution was added to stop the reaction, and then the absorbance at 450 nm was measured with an ELISA reader.

Figure 10:
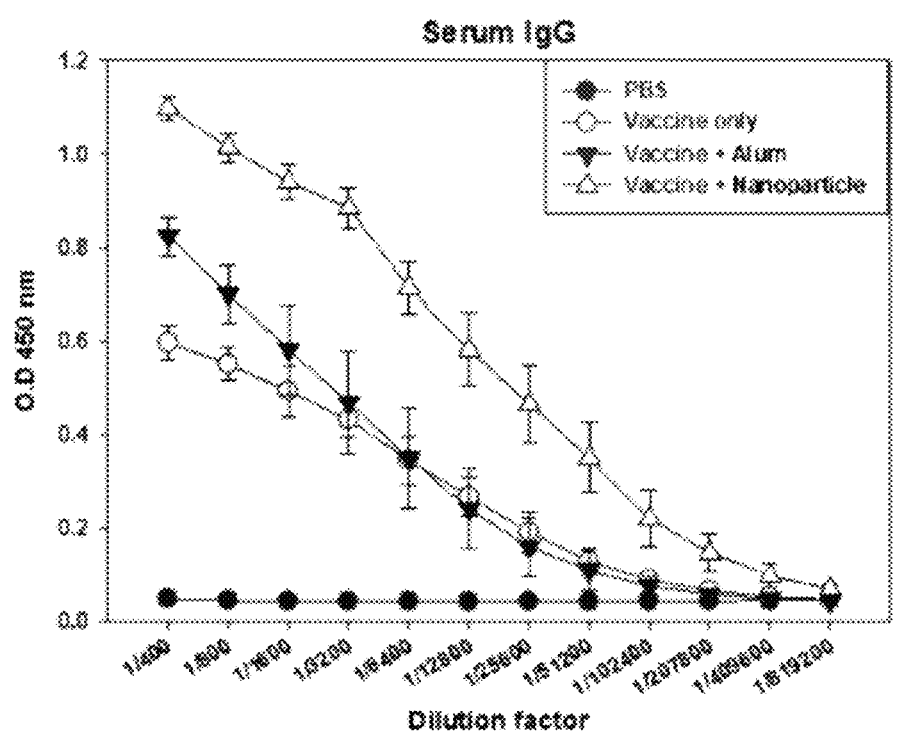
FIG. 10 shows the results of measuring vaccine antigen-specific serum IgG after injecting a mixture of an influenza vaccine antigen with poly-gamma-glutamic acid-chitosan nanoparticles into the muscle of mice in order to examine the production of an influenza vaccine antigen-specific antibody.

As a result, as shown in FIG. 10, the antibody titer against the vaccine antigen in the mice injected intramuscularly with the poly-gamma-glutamic acid-chitosan nanoparticles together with the influenza vaccine antigen was higher than the antibody titer in the mice injected intramuscularly with the influenza vaccine alone or the mixture of the influenza vaccine with alum adjuvant.

Example 10

Ability of Poly-Gamma-Glutamic Acid-Chitosan Nanoparticles to Induce Neutralizing Antibody Against Influenza Virus The measurement of the antibody titer in the sera of mice of each group was measured by an HI (hemagglutination inhibition) test method in the following manner.

All the sera were treated with a 10-fold volume of RDE (receptor-destroying enzyme) extracted from *Vibrio cholerae*, and were then incubated in an incubator at 37° C. for 18 hours. The sample obtained by removing the activities of non-specific receptors from the sera was serially 2-fold diluted by 25 µl each time in a 96-well round bottom flask. Then, the same volume of 4HAU virus (A/California/04/09 (H1N1)) was added to the serum sample and incubated at room temperature for 30 minutes. Finally, 50 µl of 0.5% turkey red blood cell-containing PBS was added to each well, and then incubated at room temperature for 30 minutes. The antibody titer was calculated in 50 µl of the diluted serum and expressed as the N value in $\log_{10} N = 10^N$.

As a result, as shown in Table 2 below, the antibody titer in the mice injected with the poly-gamma-glutamic acid-chitosan nanoparticles and the influenza vaccine antigen was about 5-6 times higher than the antibody titers in the mice injected with the influenza vaccine alone and the mice injected with the mixture of the influenza vaccine and alum adjuvant.

TABLE 2

| Vaccine adjuvants | HI GMT[a] | |
|---|---|---|
| | $1^{st}$ dose | $2^{nd}$ dose |
| Vaccine only | 43.62 (24/26) | 755.84 (26/26) |
| Vaccine + Nanoparticle | 99.02 (26/26) | 4726.46 (26/26) |
| Vaccine + Alum | 58.1 (26/26) | 980.46 (26/26) |
| PBS | <10 (0/26) | <10 (0/26) |

[a]HI antibody titer was measured in comparison with the serum of the maximum dilution concentration at which the agglutination of CA/04(H1N1) virus by 4HA unit virus is inhibited. It was expressed as the geometric average (≥10) of positive sera. The number of positive sera is indicated in parentheses (number of positive sera/total number of sera).

Example 11

Resistance of Poly-Gamma-Glutamic Acid-Chitosan Nanoparticles to Infection with Influenza Virus 14 days after the final vaccination in each group, influenza virus (A/California/04/09 (H1N1)) was administered.

For infection with the virus, test animals were anesthetized, and then 30 µl of the virus ($10^{7.25}$ $EID_{50}$) was nasally administered to each of the animal.

Figure 11:
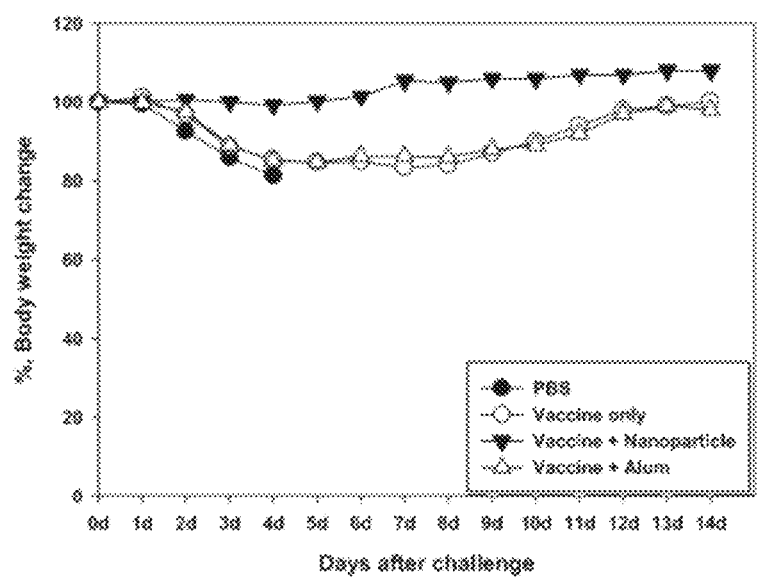
FIG. 11 is a graphic diagram showing the change in the weight of virus-infected mice over time after the intramuscular injection of a mixture of an influenza vaccine antigen with poly-gamma-glutamic acid-chitosan nanoparticles, observed in order to examine the antibody-producing ability of the mixture.
Figure 12:
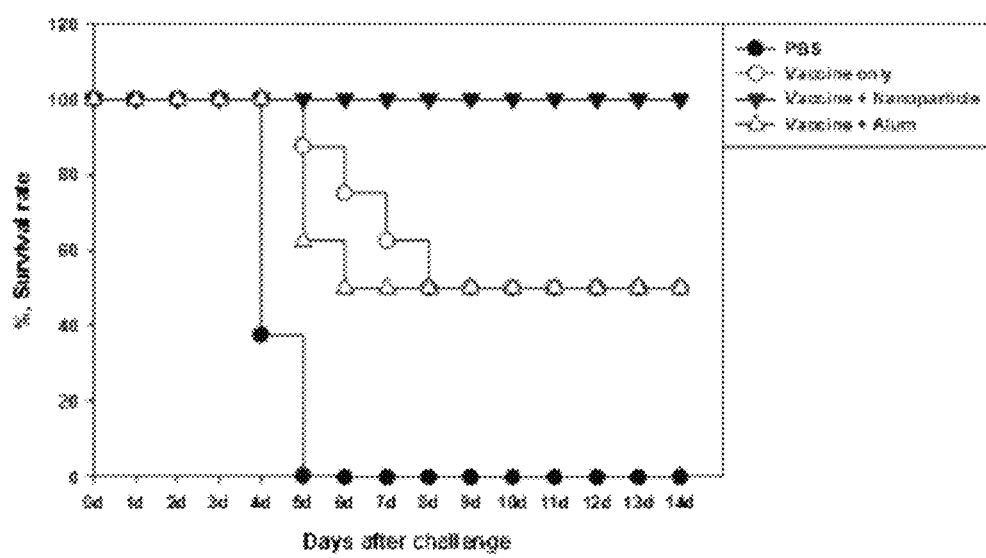
FIG. 12 is a graphic diagram showing the change in the number of deaths in virus-infected mice over time after the intramuscular injection of a mixture of an influenza vaccine antigen with poly-gamma-glutamic acid-chitosan nanoparticles, observed in order to examine the antibody-producing ability of the mixture.

As a result, as shown in FIGS. 11 and 12, in the case of the groups injected intramuscularly with the vaccine alone or the mixture of the vaccine and the alum adjuvant, the weight of the mice decreased from 2 days after infection with the virus, but in the case of the group injected with the mixture of the poly-gamma-glutamic acid-chitosan nanoparticles and the influenza vaccine, the decrease in weight caused by infection with the virus did not occur. Also, in the control group, all the mice were dead 5 days after administration of the virus, but in the group injected with the mixture of the poly-gamma-glutamic acid-chitosan nanoparticles and the influenza vaccine, all the mice survived up to 14 days after administration of the vaccine. However, in the groups administered with the vaccine alone and the mixture of the alum adjuvant and the vaccine, only 50% of the mice survived.

Thus, it was concluded that the poly-gamma-glutamic acid-chitosan nanoparticles induced the production of an antibody against the influenza vaccine to inhibit infection with the virus, whereby the mice survived.

INDUSTRIAL APPLICABILITY

The adjuvant containing the poly-gamma-glutamic acid-chitosan nanoparticles according to the present invention is prepared by simple ionic bonding between natural materials having ensured safety, and thus has little or no toxicity and side effects. Also, it can be used together with an antigen having low immunogenicity to show high antibody titer, and thus can be used in an adjuvant composition and a vaccine composition containing the adjuvant composition. In addition, the order of addition of poly-gamma-glutamic acid and chitosan can be adjusted according to the surface charge of an antigen and a virus, which are introduced, whereby the ratio of bonding between the antigen and the nanoparticles can be increased, and thus the vaccine composition can show higher antibody titers.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of increasing production of an antibody against an antigen in an animal, the method comprising:
 administering a composition comprising a complex molecule to an animal,
 the complex molecule comprising a negatively charged antigen, protonated chitosan, and poly-gamma glutamic acid,
 wherein the negatively charged antigen and the poly-gamma glutamic acid are electrostatically bound to the protonated chitosan to form the complex molecule,
 wherein the poly-gamma glutamic acid is included in the complex molecule in an amount sufficient to make the complex molecule negatively charged on its outer surface.

2. The method according to claim 1, wherein administering the composition is performed by any one method selected from the group consisting of subcutaneous injection, intramuscular injection, intracutaneous injection, intraperitoneal injection, intranasal administration, mouth administration, transdermal administration and oral administration.

3. The method according to claim 1, wherein a weight ratio between the poly-gamma-glutamic acid and the protonated chitosan is 1:1-8:1.

4. The method according to claim 1, wherein the negatively charged antigen is electrostatically bound to the protonated chitosan without crosslinking with another agent.

5. The method according to claim 1, wherein the poly-gamma-glutamic acid has a molecular weight of 50-15,000 kDa.

* * * * *